United States Patent [19]
Kidani et al.

[11] Patent Number: 6,153,646
[45] Date of Patent: Nov. 28, 2000

[54] BINUCLEAR PLATINUM COMPLEXES, METHOD FOR PREPARING SAME AND PHARMACEUTICAL COMPOSITIONS CONTAINING SAID COMPLEXES

[75] Inventors: Yoshinori Kidani, 3-13-11 Kataseyma, Fujisawa 251, Japan; Rolland-Yves Mauvernay, Lausanne, Switzerland; Teruko Irie, Tokyo, Japan

[73] Assignee: Yoshinori Kidani, Fujisawa, Japan

[21] Appl. No.: 09/147,015

[22] PCT Filed: Mar. 10, 1997

[86] PCT No.: PCT/FR97/00419

§ 371 Date: Dec. 9, 1998

§ 102(e) Date: Dec. 9, 1998

[87] PCT Pub. No.: WO97/33894

PCT Pub. Date: Sep. 18, 1997

[30] Foreign Application Priority Data

Mar. 11, 1996 [FR] France .................................. 96 03017

[51] Int. Cl.$^7$ .............................. C07F 15/00; A61K 31/28
[52] U.S. Cl. ........................... 514/492; 556/137; 560/136
[58] Field of Search ........................... 514/492; 560/136; 556/137

[56] References Cited

FOREIGN PATENT DOCUMENTS 0 214 862   9/1985   European Pat. Off. .

*Primary Examiner*—Gary L. Kunz
*Attorney, Agent, or Firm*—Oblon, Spivak, McClelland, Maier & Neustadt, P.C.

[57] ABSTRACT

A family of platinum complexes which are stable and exhibit anticancer activity.

7 Claims, 5 Drawing Sheets

BINUCLEAR PLATINUM COMPLEXES, METHOD FOR PREPARING SAME AND PHARMACEUTICAL COMPOSITIONS CONTAINING SAID COMPLEXES

BACKGROUND OF THE INVENTION

1. Field of the Invention

The present invention relates to a new class of dinuclear platinum complexes. It also relates to a process for their preparation. The invention further relates to the pharmaceutical compositions containing them and to their use for the therapeutic treatment of various cancers.

2. Description of the Background

Cisplatin and oxaliplatin are known cytostatic antineoplastic agents, which are advantageously used in the therapeutic treatment of various cancers.

Cisplatin is prescribed in particular for treating cancers of the testicles, of the ovaries, epidermoid cancers, for treating tumors of the head, of the neck, etc.

Oxaliplatin is prescribed for treating the same type of cancers, more particularly cancers of the ovaries, as well as cancers of the colon, of the upper respiratory tracts and epidermoid cancers.

Each one of these antineoplastic agents has its own specificity and, as a result, as a function of the stage of evolution of the disease, of the patient's condition or of the type of cancer to be treated, the practitioner may be led to prescribe either one of said agents. In certain cases however, the sought therapeutic effect is not reached or at least its maximum level is not reached.

Like other cytostatic antineoplastic agents, in particular other organometallic derivatives of platinum, cisplatin and oxaliplatin have an intrinsic toxicity which constitutes a serious limiting factor which the practitioner has to take into account in the prescribed treatment. In particular, cisplatin has a rather significant renal and neuromotive toxicity, all the more so as said toxicity has proved to be cumulative. It also provokes strong vomiting and can cause bradycardia, as well as myelosuppression. To a lesser degree, oxaliplatin causes a reversible sensorial dysesthesia, the effects of which can be easily reduced by suitably modulating the dose administered to the patient. But the result is that the practitioner is therapeutically limited particularly as far as curing means are concerned.

Oxaliplatin belongs to the class of platinum(II)-trans-1, 2-diaminocyclohexane complexes which are currently in full development. Said complexes, or "dach" complexes are being clinically tested in Europe, and in particular in France, as well as in the United States and Japan and they are especially efficient against melanomae and tumors of the ovaries, of the uterus, of the stomach and of the intestine, etc.

U.S. Pat. No. 4,169,846 describes such complexes, namely cisplatin(II) complexes and complexes of 1,2-diaminocyclohexane, in particular the [Pt(II)-oxalato (1R), (2R)-diaminocyclohexane] complex which is the compound known under the designation of oxaliplatin.

When said "dach" complexes are combined with 5-fluorouracile (5FU), they are particularly efficient for treating cancers of the stomach.

And when they are combined with the 5-fluorouracile and folinic acid, the "dach" complexes are especially useful for treating cancers of the colon.

Patent EP-A-143 478 relates to a method of administration of cisplatin in the form of an acid aqueous solution, and more specifically an hydrochloric acid solution having a pH preferably comprised between 3.2 and 3.5 and containing chloride ions for example from sodium chloride for stabilizing the solution and thus avoiding hydrolysis.

U.S. Pat. No. 4,177,263 which also relates to cisplatin, describes a method for treating cancer tumors in animals, which method consists in injecting by parenteral route a complex platinum agent in an efficient quantity for causing regression of the tumor.

Clinical tests conducted in France on the use of the combination of oxaliplatin with cisplatin have shown the remarkable effect of such combination on the cancer of the liver. However, it has been found that there are problems of stability with the combined complexes.

International patent application WO 94/12193 describes in particular a composition intended for the joint administration of cisplatin and oxaliplatin as a combination after extemporaneous reconstitution by addition of aqueous liquid in the form of a lyophilisate containing the cisplatin and the oxaliplatin in a weight ratio comprised between 2:1 and 1:2.

SUMMARY OF THE INVENTION

A new family of platinum complexes has now been found, which complexes are very stable and have an anticancer activity.

The new complexes of the invention have one of the general formulae (I) or (II):

$$\left[ (Y-Y)-Pt(II) \underset{X}{\overset{X}{\diagup}} \underset{A_2}{\overset{A_1}{\diagdown}} Pt(II) \right]^{2+} (Ld)^{2-} \quad (I)$$

$$\left[ (Y-Y)- \underset{Hal}{\overset{Hal}{\vert}} Pt(IV) \underset{X}{\overset{X}{\diagup}} \underset{A_2}{\overset{A_1}{\diagdown}} Pt(II) \right]^{2+} (Ld)^{2-} \quad (II)$$

in which:

Y—Y is an amine bidentate ligand of formula
  $NH_2—R_1—NH_2$ in which $R_1$ is a $C_2$–$C_6$ linear or branched alkylene group or an o-phenylene group;
  or a group of formula $$(CH_2)_n \diagup \underset{(CH_2)_l NH_2}{\overset{(CH_2)_m NH_2}{\diagdown}}$$

in which n=2, 3, 4, 5
  m=0, 1,
  and l=0, 1;

$A_1$ and $A_2$ represent either two ammine identical monodentate ligands, n-isopropylamine or ($C_3$–$C_7$) cycloalkylamine, or they are bonded together and form an amine bidentate ligand of formula:
  $NH_2—R_1—NH_2$ in which $R_1$ is a $C_2$–$C_6$ linear or branched alkylene group or an o-phenylene group;

or a group of formula in which n=2, 3, 4, 5
m=0, 1,
and I=0, 1;

X represents a bridging ligand between the two platinums selected among Cl, Br, F and I;

the dissociable Ld group represents:
   either two monodentate B ligands selected among $NO_3$ or R COOH, in which R is a gluconic or glucoronic acid residue;
   or the bidentate B—B ligand selected among in which R is hydrogen, the methyl, ethyl, phenyl, benzyl group;

Hal is a halogen atom selected among Cl, Br, F and I.

A family of preferred compounds of the invention are the compounds of formula (I) or (II) in which:

Y—Y represents a bidentate ligand selected among ethylenediamine, o-phenylenediamine, trimethylenediamine, 1,2-cyclohexanediamine and 2-(aminomethyl) cyclohexylamine;

X is Cl;

$A_1$ and $A_2$ represent either two ammino monodentate ligands or they are bonded together and form a bidentate ligand selected among ethylenediamine, o-phenylenediamine, trimethylenediamine, 1,2-cyclohexanediamine and 2-(aminomethyl) cyclohexylamine;

Ld is:
   either two monodentate B ligands selected among $NO_3$ or RCOOH, in which R is a gluconic or glucoronic acid residue;
   or a bidentate B—B ligand selected among dicarboxylate, $SO_4$, oxalate, malonate, 1,1-cyclobutanedicarboxylate;

Hal is Cl.

The invention also relates to a process for the preparation of the new dinuclear platinum complexes, characterized in that said process consists in reacting in an aqueous solution and in equimolar proportion two mononuclear platinum complexes, one of which is a di-halogenated platinum complex C1 and the other a platinum complex C2 comprising either two monodentate B ligands or one bidentate B—B ligand as defined above, such that a bridge forms between the two complexes, in which X is as defined above.

According to a preferred embodiment of the invention, the process consists in:

a) dissolving in distilled water a mononuclear platinum complex C1 by heating in a water-bath;

b) dissolving like in step a) the mononuclear platinum complex C2 in distilled water;

c) mixing the two solutions and boiling the reaction mixture at 80° C.;

d) leaving the reaction mixture at room temperature; and e) filtering, washing the needle- or feather-shaped pale yellow crystalline precipitate resulting from step d) with warm water and then with alcohol;

In step d), the alcohol used is advantageously ethanol.

The examples of mononuclear complexes C1 and C2 are the following mononuclear platinum complexes:

Complexes C1
   the cisplatin [Pt(II)-cis $Cl_2$ $(NH_3)_2$], hereafter "DDP",
   the complex [Pt(II)-$Cl_2$ (1S),(2S)-diaminocyclohexane], hereafter "d-DC dach",
   the complex [Pt(II)-$Cl_2$ (1R),(2R)-diaminocyclohexane], hereafter "l-DC dach",
   the complex [Pt(II)-$Cl_2$ (1R),(2S)-diaminocyclohexane], hereafter "cis-DC dach",
   the complex [Pt(IV)-oxalato trans $Cl_2$ (1R),(2R)-diaminocyclohexane ], hereafter "l-OHP.Cl".

Complexes C2
   the oxaliplatin: [Pt(II)-oxalato (1R),(2R)-diaminocyclohexane], hereafter "l-OHP",
   the complex [Pt(II)-oxalato (1R),(1S)-diaminocyclohexane], hereafter "cis-OHP",
   the complex [Pt(II)-$(NO_3)_2$ (1R),(2R)-diaminocyclohexane], hereafter "l-DN dach",
   the complex [Pt(II)-$(NO_3)_2$ (1S),(2S)-diaminocyclohexane], hereafter "d-DN dach",
   the complex [Pt(II)-$(NO_3)_2$ (1R),(2S)-diaminocyclohexane], hereafter "cis-DN dach",
   the carboplatin [Pt(II)-cis-diammine 1,1-cyclobutanedicarboxylate], hereafter "CBDCA",
   the complex [Pt(IV)-oxalato trans $Cl_2$ (1R),(2R)-diaminocyclohexane ], hereafter "l-OHP.Cl".

The mononuclear platinum complexes C1 and C2 are advantageously oxaliplatin and cisplatin.

The compounds of the present invention of formula (I) are active principles of pharmaceutical compositions whose toxicity is compatible with their use as medicaments.

Thus, according to another aspect thereof, the present invention relates to pharmaceutical compositions containing a dinuclear platinum complex of formula (I) or (II) as the active principle.

The compounds of the present invention are administered in unit dosage form. The unit dosage forms are formulated in pharmaceutical compositions in which the active principle is mixed with a pharmaceutical vehicle.

The pharmaceutical compositions containing the dinuclear platinum complex of the invention, as the active principle, may be administered orally or parenterally (intramuscularly or intravenously).

For oral administration, the pharmaceutical compositions may be in the form of tablets, gelatin capsules, powders, granules or any other form which may be administered orally. The pharmaceutical compositions may further contain pharmaceutically acceptable vehicles that are compatible with the compounds of the invention.

The pharmaceutical compositions are preferably administered parenterally (intramuscularly—intravenously). The injectable solutions are aqueous solutions containing at least a pharmaceutically acceptable acid buffer free from any chloride ions and a neutral substance for the vehicle.

Preferably, the pH of the injectable solution is adjusted to a value comprised preferably between 6.8 and 7.

According to the invention, inorganic or organic acids and their pharmaceutically acceptable alkaline salts, free from any chloride ions, are advantageously used, as the acid buffer.

More particularly, an acid or a mixture of pharmaceutically acceptable corresponding organic acids and alkaline salts are used. As the organic acid, a dicarboxylic amino acid, such as aspartic or glutamic acid is preferably used and as the alkaline salt, a corresponding lithium, sodium or potassium salt is used. As the inorganic acid, acetic acid or phosphoric acid may be used, for example.

As the preferential acid buffer, the glutamic acid is used in the presence or absence of sodium glutamate.

According to the invention, the composition further generally comprises a neutral substance acting as the vehicle, such as a carbohydrate like the lactose, glucose, mannitol or sorbitol or similar compounds.

Said solution may thus be administered parenterally, if necessary, together with other cytostatic agents which are physico-chemically compatible with the dinuclear platinum complexes of the invention and in accordance with the current practices of anticancerous therapy.

The compounds of the present invention have an antitumor activity against experimental tumors in rats, such as L 1210 and are thus particularly useful in tumor chemotherapy.

According to another one of its aspects, the present invention relates to the use of the products of formula (I) for the preparation of medicaments intended to treat various cancers.

PHARMACOLOGICAL STUDY: ANTITUMOR ACTIVITY

The antitumor activity of the compounds of the invention was demonstrated by the following test.

EXPERIMENT $10^5$ leukemia cells L 1210 of mice in a saline suspension were injected intraperitoneally to groups of 6 mice CDF1 on day 0. The compound to be tested was administered intraperitoneally 1, 3 and 5 days after transplanting cancerous cells.

Control groups of 6 mice were also constituted but were not administered with the compounds to be tested.

The therapeutical effectiveness of the compounds of the invention was measured by the ratio T/C %. This ratio represents 100 times the average survival time of the group administered with the compound to be tested divided by the average survival time of the control group which was not administered with the compound to be tested.

The results are shown in tables 1 and 2 below:

TABLE 1

Antitumor activity of the complex of the invention: the dinuclear platinum complex of oxaliplatin and of cisplatin (I-OHP.DDP) compared with the activity of the compounds of the prior art: cisplatin (DDP), oxaliplatin (I-OHP) and oxaliplatin/cisplatin (I-OHP + DDP) combination against cancerous cells L 1210.

| | T/C (%) Dose (mg/kg) | | | |
|---|---|---|---|---|
| | 12,5 | 6,25 | 3,12 | 1,56 |
| DDP | 78 | 245 | 226 | 124 |
| I-OHP | 308 (4/6) | 253 (1/6) | 211 (1/6) | 158 |
| I-OHP + DDP (1:1) | | 230 (1/6) | 284 (2/6) | 167 |
| I-OHP · DDP | 234 (1/6) | 347 (3/6) | 378 (5/6) | 183 |

The numbers in brackets represent the number of mice cured in a group of 6 mice.

TABLE 2

Antitumor activity of the complex of the invention (I-OHP.DDP) compared with the activity of the known combination I-OHP + DDP against cancerous cells L 1210 which have been treated with DDP beforehand.

| | T/C (%) Dose (mg/kg) | | |
|---|---|---|---|
| | 6.25 | 3.12 | 1,56 |
| I-OHP + DDP | 105 | 113 | 103 |
| I-OHP · DDP | 207 (2/6) | 398 (5/6) | 345 (6/6) |

The numbers in brackets represent the number of mice cured in a group of 6 mice.

The results collated in tables 1 and 2 show the effectiveness of the dinuclear platinum complex of the invention as an antitumor agent. Indeed, at an effective dose of 3.12 mg/kg, the complex of the invention enabled 5 mice out of 6 to recover against 2 out of 6 for the oxaliplatin/cisplatin combination and 1 out of 6 for the oxaliplatin (Table 1), it being understood that a lesser dose is not sufficient and that a greater dose is toxic.

Furthermore, it is noted that the leukemia cells L 1210 are previously treated with cisplatin, the complex of the invention is very effective at a dose of 1.56 mg/kg: 6 mice out of 6 have recovered whereas the known combination is not at all effective (table 2).

STABILITY

Moreover, the stability of the dinuclear platinum complexes of the invention was checked by paper chromatography.

The stability was indeed assessed by the values of the characteristic Rf:

$$Rf = \frac{\text{distance travelled by the compound}}{\text{distance travelled by the mobile solvent}}$$

Rf is obtained by paper chromatography (filter paper Toyo 2×20 cm) at room temperature using some $SnCl_2$ as the detector.

The results are shown in Table 3 below:

The products of the invention are identified below by a code number NCU which is attributed by the inventors.

TABLE 3

| NCU | Complexes | Rf Eluant solvant | |
| --- | --- | --- | --- |
| | | 20% Methanol | 20% Ethanol |
| 501 | l-OHP · DDP | 0,64 | 0,55 |
| — | l-OHP · DDP* | 0,64 | 0,55 |
| 502 | d-OHP · DDP | 0,62 | 0,52 |
| 503 | cis-OHP · DDP | 0,72 | 0,70 |
| 504 | l-OHP · l-DC dach | 0,68 | 0,38 |
| 507 | DDP · l-DN dac | 0,69 | 0,64 |
| 510 | L-DN dach · l-DC dach | — | 0,72 |
| 513 | DDP · CBDCA | 0,69 | 0,59 |
| 514 | l-OHP · Cl · DDP | 0,73 | 0,73 |
| — | DDP | 0,80 | 0,57 |
| — | l-OHP | 0,65 | 0,63 |
| — | d-OHP | 0,67 | 0,60 |
| — | cis-OHP | 0,70 | 0,65 |
| — | CBDCA | 0,76 | 0,74 |
| — | PtCl$_2$(l-dach) | — | 0,74 |
| — | Pt(NO$_3$)$_2$(l-dach) | — | 0,13 |

*the compound labelled with this asterisk has undergone heating in some HCl 1N

The invention shall now be illustrated more precisely by the following illustrating and non-limiting examples:

EXAMPLE 1

Synthesis of a dinuclear platinum complex of l-OHP and cisplatin: [(cis-diammine) (1R),(2R)-diaminocyclohexane-$\mu$-dichloro-di-Pt(II)] oxalate or else [(NH$_3$)$_2$Pt ($\mu$-Cl)$_2$ Pt (trans-l-dach)] ox, hereafter l-OHP.DDP: NCU 501 of chemical structure:

0.60 g (2 mmol) of cisplatin (molar mass=299 g/mol) is dissolved in 90 ml of distilled water by heating in a water-bath (pH≈5.0). 0.80 g (2 mmol) of l-OHP (molar mass=397 g/mol) is dissolved in 80 ml of distilled water by heating in a water-bath (pH≈5.0). Both solutions are combined and then the reaction mixture is boiled to 80° C. After 15–30 minutes, a needle-shaped pale yellow precipitate is obtained. The precipitate is filtered, washed with warm water and then with alcohol. 0.61 g of the pale yellow crystalline complex is thus obtained with a yield of 87%.

Figure 1:
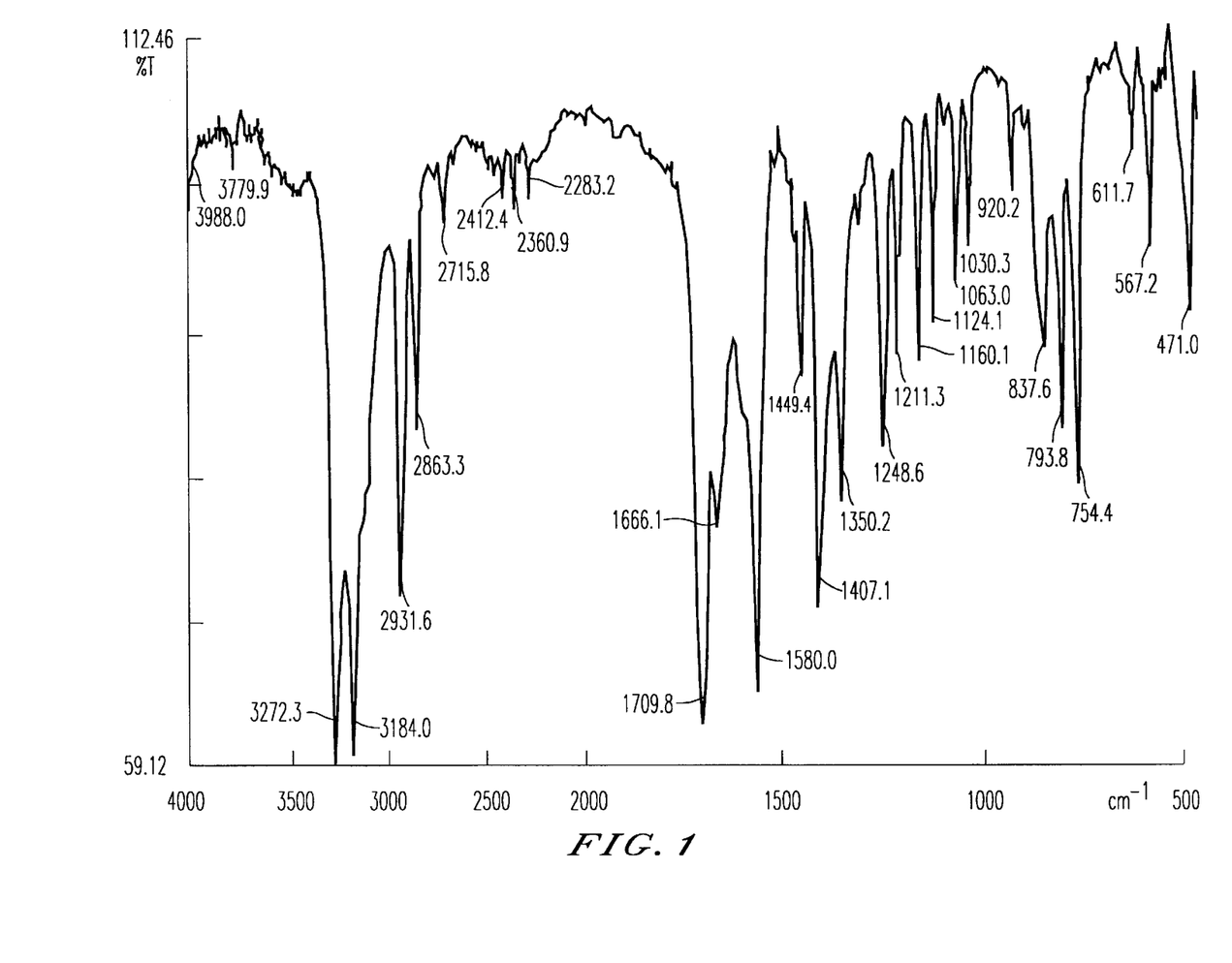
FIG. 1 is an infrared spectrum of the platinum complex: [(cis-diammine) (1R),(2R)- diaminocyclohexane-µ-dichloro-di-Pt(II)] oxalate.

The infrared absorption spectrum of this complex is represented in FIG. 1.

Elemental analysis: C$_8$H$_{20}$N$_4$O$_4$Pt$_2$Cl$_2$ (molar mass = 697 g/mol).

| | Calculated | Found |
| --- | --- | --- |
| C | 13,77% | 13,98% |
| H | 2,86% | 3,08% |
| N | 8,03% | 8,06% |
| Pt | 55,95% | 52,9% |

EXAMPLE 2

Synthesis of a dinuclear platinum complex of d-OHP and cisplatin: [(cis-diammine) (1S), (2S)-diaminocyclohexane-$\mu$-dichloro-di-Pt(II)] oxalate or else [(NH$_3$)$_2$Pt ($\mu$-Cl)$_2$ Pt (trans-d-dach)] Ox, hereafter d-OHP.DDP: NCU 502.

0.60 g (2 mmol) of cisplatin is dissolved in 90 ml of distilled water by heating in a water-bath (pH≈5.0). 0.80 g (2 mmol) of d-OHP is also dissolved in 80 ml of distilled water by heating in a water-bath (pH≈5.0). Both solutions are combined and then the reaction mixture is boiled at 80° C. After 15–30 minutes, a needle-shaped pale yellow precipitate is obtained. The precipitate is filtered, washed with warm water and then with alcohol. 0.60 g of the expected pale yellow crystalline complex is thus obtained with a yield of 86%.

Figure 2:
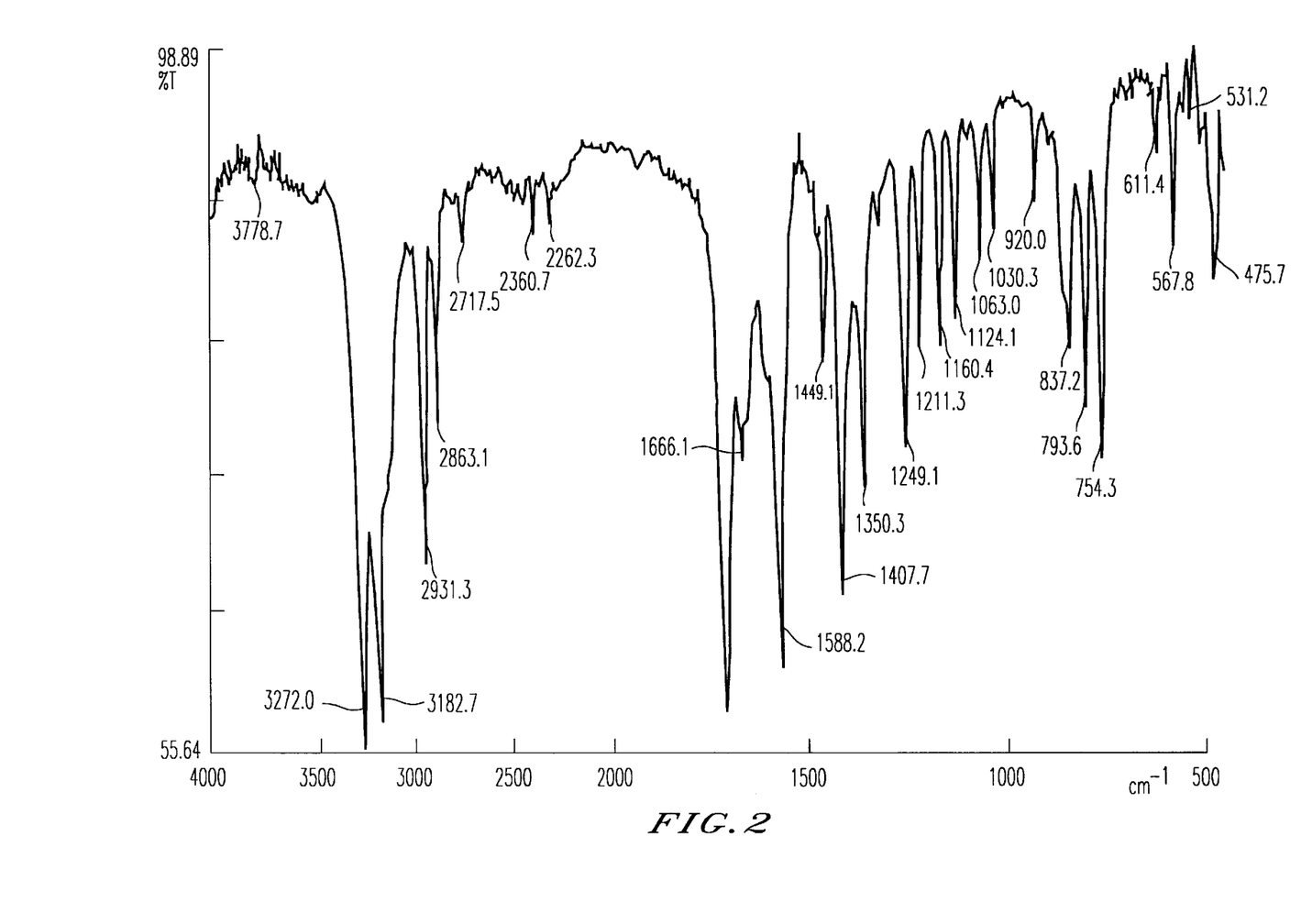
FIG. 2 is an infrared spectrum of the platinum complex: [(cis-diammine) (1S),(2S)- diaminocyclohexane-µ-dichloro-di-Pt(II)] oxalate.

The infrared absorption spectrum is represented in FIG. 2.

Elemental analysis: C$_8$H$_{20}$N$_4$O$_4$Pt$_2$Cl$_2$ (molar mass = 697 g/mol).

| | Calculated | Found |
| --- | --- | --- |
| C | 13,77% | 13,60% |
| H | 2,86% | 2,96% |
| N | 8,03% | 8,09% |
| Pt | 55,95% | — |

EXAMPLE 3

Synthesis of a dinuclear platinum complex of cis-OHP and of cisplatin: [(cis-diammine) (R),(S)-diaminocyclohexane-$\mu$-dichloro-di-Pt(II)] oxalate or else [(NH$_3$)$_2$Pt ($\mu$-Cl)$_2$ Pt (cis-dach)] Ox, hereafter cis-OHP.DDP: NCU 503.

0.60 g (2 mmol) of cisplatin is dissolved in 90 ml of distilled water by heating in a water-bath (pH≈5.0). 0.80 g (2 mmol) of cis-OHP is also dissolved in 80 ml of distilled water by heating in a water-bath (pH≈5.0). Both solutions are combined and then again heated for one hour. After concentrating the solution at ⅓–½ of its initial volume and leaving the mixture at room temperature, needle-shaped pale yellow crystals are obtained. The crystals are filtered, washed with warm water and then with alcohol. 0.61 g of the expected needle-shaped pale yellow crystalline complex is thus obtained with a yield of 87%.

Figure 3:
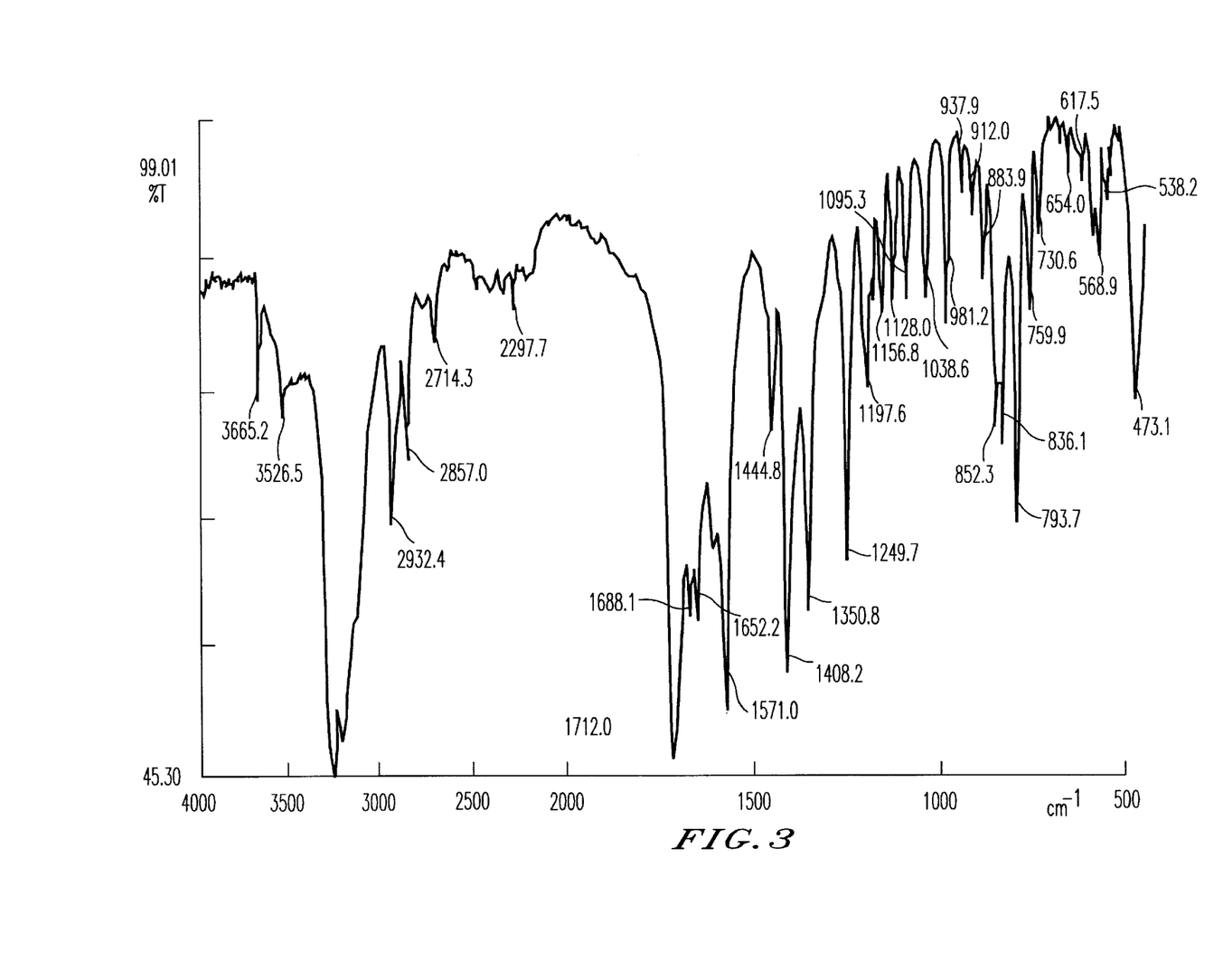
FIG. 3 is an infrared spectrum of the platinum complex: [(cis-diammine) (R),(S)- diaminocyclohexane-µ-dichloro-di-Pt(II)] oxalate.

The infrared absorption spectrum is represented in FIG. 3.

Elemental analysis: C$_8$H$_{20}$N$_4$O$_4$Pt$_2$Cl$_2$ (molar mass = 696 g/mol).

| | Calculated | Found |
| --- | --- | --- |
| C | 13,77% | 13,78% |
| H | 2,86% | 2,90% |
| N | 8,03% | 8,03% |
| Pt | 55,95% | — |

EXAMPLE 4

Synthesis of a dinuclear platinum complex of l-OHP and of l-DC dach: [bis(1R),(2R)-diaminocyclohexane-$\mu$-dichloro-di-Pt(II)] oxalate or else [(trans-l-dach) Pt ($\mu$-Cl)$_2$Pt (trans-l-dach)] Ox, hereafter l-OHP.DC dach: NCU 504.

0.40 g (1 mmol) of l-OHP is dissolved in 40 ml of distilled water by heating in a water-bath. 0.38 g (1 mmol) of l-DC dach (molar mass=379 g/mol) is also dissolved in 300 ml of distilled water by heating in a water-bath. Both solutions are combined and then the reaction mixture is boiled for 1 hour. After the reaction mixture has been left to rest at room temperature, needle-shaped pale yellow crystals are obtained. After filtration, the crystals are washed with warm water and then with alcohol. 0.30 g of the expected needle-shaped pale yellow crystalline complex is thus obtained with a yield of 39%.

| Elemental analysis: $C_{14}H_{28}N_4O_4Pt_2Cl_2$ (molar mass = 777 g/mol). | | |
|---|---|---|
| | Calculated | Found |
| C | 21,62% | 20,82% |
| H | 3,60% | 3,84% |
| N | 7,20% | 7,38% |
| Pt | 50,19% | — |

EXAMPLE 5

Synthesis of a dinuclear platinum complex of I-OHP and of d-DC dach: [(1R), (2R)-diaminocyclohexane (1S),(2S)-diaminocyclohexane-µ-dichloro-di-Pt(II)] oxalate or else [(trans-I-dach) Pt (µ-Cl)$_2$Pt (trans-d-dach)] Ox, hereafter I-OHP.d-DC dach: NCU 505.

0.40 g (1 mmol) of I-OHP is dissolved in 40 ml of distilled water by heating in a water-bath and 0.38 g (1 mmol) of d-DC dach (molar mass=379 g/mol) is similarly dissolved in 300 ml of distilled water. Both solutions are combined and then the reaction mixture is boiled for 1 hour. After the reaction mixture has been left to rest at room temperature, needle-shaped pale yellow crystals are obtained. After filtration, the crystals are washed with warm water and then with alcohol. 0.30 g of the crystalline complex is thus obtained with a yield of 39%.

| Elemental analysis: $C_{14}H_{28}N_4O_4Pt_2Cl_2$ (molar mass = 777 g/mol). | | |
|---|---|---|
| | Calculated | Found |
| C | 21,62% | 21,52% |
| H | 3,60% | 3,99% |
| N | 7,20% | 7,05% |
| Pt | 50,19% | — |

EXAMPLE 6

Synthesis of a dinuclear platinum complex of I-OHP and of cis-DC dach: [(1R),(2R)-diaminocyclohexane (R),(S)-diaminocyclohexane-µ-dichloro-di-Pt(II)] oxalate or else [(trans-I-dach) Pt (µ-Cl)$_2$Pt (cis-dach)] Ox, hereafter I-OHP.cis DC dach: NCU 506.

0.40 g (1 mmol) of I-OHP is dissolved in 40 ml of distilled water by heating in a water-bath. 0.38 g (1 mmol) of cis-DC dach (molar mass=379 g/mol) is similarly dissolved in 300 ml of distilled water. Both solutions are combined and then the reaction mixture is boiled for approximately 1 hour. After the reaction mixture has been left to rest at room temperature, needle-shaped pale yellow crystals are obtained. The precipitate is filtered, washed with warm water and then with alcohol. 0.28 g of the expected needle-shaped yellow crystalline complex is thus obtained with a yield of 36%.

| Elemental analysis: $C_{14}H_{28}N_4O_4Pt_2Cl_2$ (molar mass = 777 g/mol). | | |
|---|---|---|
| | Calculated | Found |
| C | 21,62% | 20,91% |
| H | 3,60% | 3,55% |
| N | 7,20% | 7,05% |
| Pt | 50,19% | — |

EXAMPLE 7

Synthesis of a dinuclear platinum complex of cisplatin and of I-DN dach: [(cis-diammine) (1R),(2R)-diaminocyclohexane-µ-dichloro-di-Pt(II)] Nitrate or else [(NH$_3$)$_2$ Pt (µ-Cl)$_2$Pt(trans-I-dach)] (NO$_3$)$_2$, hereafter DDP.I-DN dach: NCU 507.

0.299 g (1 mmol) of cisplatin is dissolved in 50 ml of distilled water by heating in a water-bath ((pH about 5.0). 0.433 g (1 mmol) of I-DN dach (molar mass=433 g/mol) is similarly dissolved in 20 ml of distilled water. Both solutions are combined and then the reaction mixture is boiled. After approximately 30 minutes, a feather-shaped very pale yellow crystalline precipitate is obtained. The precipitate is filtered, washed with warm water and then with alcohol. 0.30 g of the expected crystalline complex is thus obtained with a yield of 36%.

| Elemental analysis: $C_6H_{20}N_6O_6Pt_2Cl_2$ (molar mass = 829 g/mol). | | |
|---|---|---|
| | Calculated | Found |
| C | 20,26% | 19,75% |
| H | 2,41% | 2,78% |
| N | 10,13% | 10,29% |
| Pt | 47,04% | — |

EXAMPLE 8

Synthesis of a dinuclear platinum complex of cisplatin and of d-DN dach: [(cis-diammine) (1S),(2S)-diaminocyclohexane-µ-dichloro-di-Pt(II)] Nitrate or else [(NH$_3$)$_2$ Pt (µ-Cl)$_2$Pt(trans-d-dach)] (NO$_3$)$_2$, hereafter DDP.d-DN dach: NCU 508.

0.299 g (1 mmol) of cisplatin is dissolved in 50 ml of distilled water by heating in a water-bath ((pH about 5.0). 0.433 g (1 mmol) of d-DN dach (molar mass=433 g/mol) is similarly dissolved in 20 ml of distilled water. Both solutions are combined and then the reaction mixture is boiled. After approximately 30 minutes, a feather-shaped very pale yellow crystalline precipitate is obtained. The precipitate is filtered, washed with warm water and then with alcohol. 0.28 g of the expected crystalline complex is thus obtained with a yield of 34%.

| Elemental analysis: $C_6H_{20}N_6O_6Pt_2Cl_2$ (molar mass = 829 g/mol). | | |
|---|---|---|
| | Calculated | Found |
| C | 20,26% | 20,16% |
| H | 2,41% | 2,31% |
| N | 10,13% | 10,03% |
| Pt | 47,04% | — |

EXAMPLE 9

Synthesis of a dinuclear platinum complex of cisplatin and of cis-DN dach: [(cis-diammine) (R),(S)-diaminocyclohexane-µ-dichloro-di-Pt(l)] Nitrate or else [(NH$_3$)$_2$ Pt (µ-Cl)$_2$Pt(cis-dach)] (NO$_3$)$_2$, hereafter DDP.cis-DN dach: NCU 509.

0.299 g (1 mmol) of cisplatin is dissolved in 50 ml of distilled water by heating in a water-bath ((pH about 5.0). 0.433 g (1 mmol) of cis-DN dach (molar mass=433 g/mol) is similarly dissolved in 20 ml of distilled water. Both solutions are combined and then the reaction mixture is boiled. After approximately 30 minutes, a feather-shaped very pale yellow crystalline precipitate is obtained. The precipitate is filtered, washed with warm water and then with alcohol. 0.28 g of the expected crystalline complex is thus obtained with a yield of 34%.

Elemental analysis: $C_6H_{20}N_6O_6Pt_2Cl_2$ (molar mass = 829 g/mol).

|    | Calculated | Found  |
|----|------------|--------|
| C  | 20,26%     | 20,05% |
| H  | 2,41%      | 2,25%  |
| N  | 10,13%     | 10,01% |
| Pt | 47,04%     | —      |

EXAMPLE 10

Synthesis of a dinuclear platinum complex of I-DC dach and of I-DN dach: [bis(1R), (2R)-diaminocyclohexane-$\mu$-dichloro-10 di-Pt(II)] Nitrate or else [(trans-I-dach) Pt ($\mu$-Cl)$_2$Pt(trans-I-dach)] (NO$_3$)2], hereafter I-DC dach.I-DN dach: NCU 510.

0.38 g (1 mmol) of I-DC dach is dissolved in 300 ml of distilled water by heating in a water-bath ((pH about 5.0). 0.433 g (1 mmol) of I-DN dach (molar mass=433 g/mol) is similarly dissolved in 20 ml of distilled water. Both solutions are combined and then the reaction mixture is boiled. After approximately 30 minutes, a feather-shaped very pale yellow crystalline precipitate is obtained. The crystals are filtered, washed with warm water and then with alcohol. 0.20 g of the expected crystalline complex is thus obtained with a yield of 25%.

Elemental analysis: $C_{12}H_{28}N_6O_6Pt_2Cl_2$ (molar mass = 813 g/mol).

|    | Calculated | Found  |
|----|------------|--------|
| C  | 17,71%     | 18,05% |
| H  | 3,44%      | 3,40%  |
| N  | 10,33%     | 9,79%  |
| Pt | 47,37%     | —      |

EXAMPLE 11

Synthesis of a dinuclear platinum complex of d-DC dach and of I-DN dach: [(1R),(2R)-diaminocyclohexane (1S), (2S)-diaminocyclohexane-$\mu$-dichloro-di-Pt(II)] Nitrate or else

[(trans-I-dach) Pt ($\mu$-Cl)$_2$Pt(trans-d-dach)] (NO$_3$)2], hereafter d-DC dach.I-DN dach: NCU 511.

0.38 g (1 mmol) of d-DC dach is dissolved in 300 ml of distilled water by heating in a water-bath (pH about 5.0). 0.433 g (1 mmol) of I-DN dach (molar mass=433 g/mol) is similarly dissolved in 20 ml of distilled water. Both solutions are combined and then the reaction mixture is boiled. After approximately 30 minutes, a feather-shaped very pale yellow crystalline precipitate is obtained. These crystals are filtered, washed with warm water and then with alcohol. 0.20 g of the expected crystalline complex is thus obtained with a yield of 25%.

Elemental analysis: $C_{12}H_{28}N_6O_6Pt_2Cl_2$ (molar mass = 813 g/mol).

|    | Calculated | Found  |
|----|------------|--------|
| C  | 17,71%     | 17,65% |
| H  | 3,44%      | 3,34%  |
| N  | 10,133%    | 10,30% |
| Pt | 47,97%     | —      |

EXAMPLE 12

Synthesis of a dinuclear platinum complex of cis-DC dach and of I-DN dach: [(1R),(2R)-diaminocyclohexane (R),(S)-diaminocyclohexane-$\mu$-dichloro-di-Pt(II)] Nitrate or else [(trans-I-dach) Pt ($\mu$-Cl)$_2$Pt(cis-dach)] (NO$_3$)$_2$], hereafter cis-DC dach.I-DN dach: NCU 512.

0.38 g (1 mmol) of cis-DC dach is dissolved in 300 ml of distilled water by heating in a water-bath ((pH about 5.0). 0.433 g (1 mmol) of I-DN dach (molar mass=433 g/mol) is similarly dissolved in 20 ml of distilled water. Both solutions are combined and then the reaction mixture is boiled for 30 minutes. After the solution has been concentrated at 50% of its initial volume, the mixture is left to rest at room temperature. A needle-shaped very pale yellow crystalline precipitate is obtained. These crystals are filtered, washed with warm water and then with alcohol. 0.15 g of the expected crystalline complex is thus obtained with a yield of 18%.

Elemental analysis: $C_{12}H_{28}N_6O_6Pt_2Cl_2$ (molar mass = 813 g/mol).

|    | Calculated | Found  |
|----|------------|--------|
| C  | 17,71%     | 18,01% |
| H  | 3,44%      | 3,45%  |
| N  | 10,33%     | 10,23% |
| Pt | 47,97%     | —      |

EXAMPLE 13

Synthesis of a dinuclear.platinum complex of DDP and CBDCA: [bis (cis-diammine)-$\mu$-dichloro-di-Pt(II)] 1,1-cyclobutanedicarboxylate, or else [(NH$_3$)$_2$Pt ($\mu$-Cl)$_2$Pt(NH$_3$)$_2$] CBDCA, hereafter DDP.CBDCA: NCU 513.

0.30 g (1 mmol) of DDP is dissolved in 50 ml of distilled water by boiling. 0.37 g (1 mmol) of CBDCA and a drop of HCl 1N are then added to the reacture medium and the mixture is boiled again for 30 minutes. After approximately 30 minutes, needle-shaped yellowish brown crystals are obtained. These crystals are filtered, washed with hot water and then with alcohol. 0.50 g of the expected crystalline complex is thus obtained with a yield of 75%.

Figure 4:
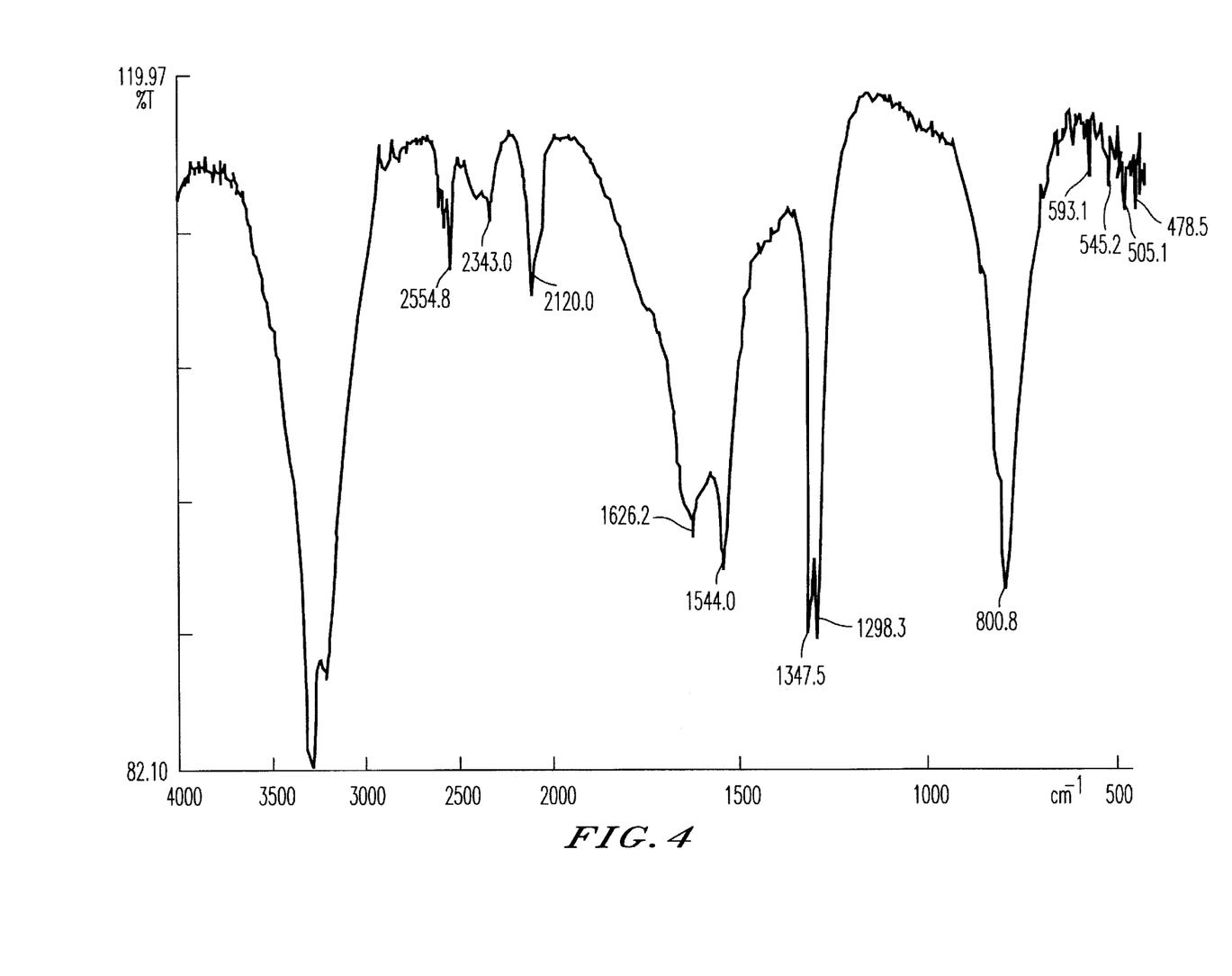
FIG. 4 is an infrared spectrum of the platinum complex: [bis (cis-diammine)-µ- dichloro-di-Pt(II)] 1,1-cyclobutanedicarboxylate.

The infrared absorption spectrum is represented in FIG. 4.

Elemental analysis: $C_6H_{12}N_4O_4Pt_2Cl_2$ (molar mass = 671 g/mol).

|    | Calculated | Found  |
|----|------------|--------|
| C  | 10,73%     | 10,18% |
| H  | 2,68%      | 2,14%  |
| N  | 8,34%      | 8,33%  |
| Pt | 58,12%     | —      |

EXAMPLE 14

Synthesis of a dinuclear platinum complex of I-OHP.Cl and of DDP: [(cis-diammine) (trans-dichloro) (1R),(2R)-diaminocyclohexane-$\mu$-dichloro-Pt(II)-Pt(IV)] Oxalate or else [(NH$_3$)$_2$Pt (II) ($\mu$-Cl)$_2$ Pt(IV) (trans-Cl$_2$-trans-I-dach)] Ox, hereafter I-OHP.Cl-DDP: NCU 514.

0.47 g (1 mmol) of I-OHP.Cl (molar mass=469 g/mol) is dissolved in 50 ml of distilled water by heating in a water-bath and 0.3 g (1 mmol) of DDP (molar mass=299 g/mol) is similarly dissolved in 30 ml of distilled water. Both solutions are combined and then the reaction mixture is boiled for 30 minutes. When the reaction is completed, very pale yellow crystalline precipitates are obtained. The precipitates are filtered, washed with warm water and then with alcohol. 0.33 g of the expected crystalline complex is thus obtained with a yield of 50%.

Figure 5:
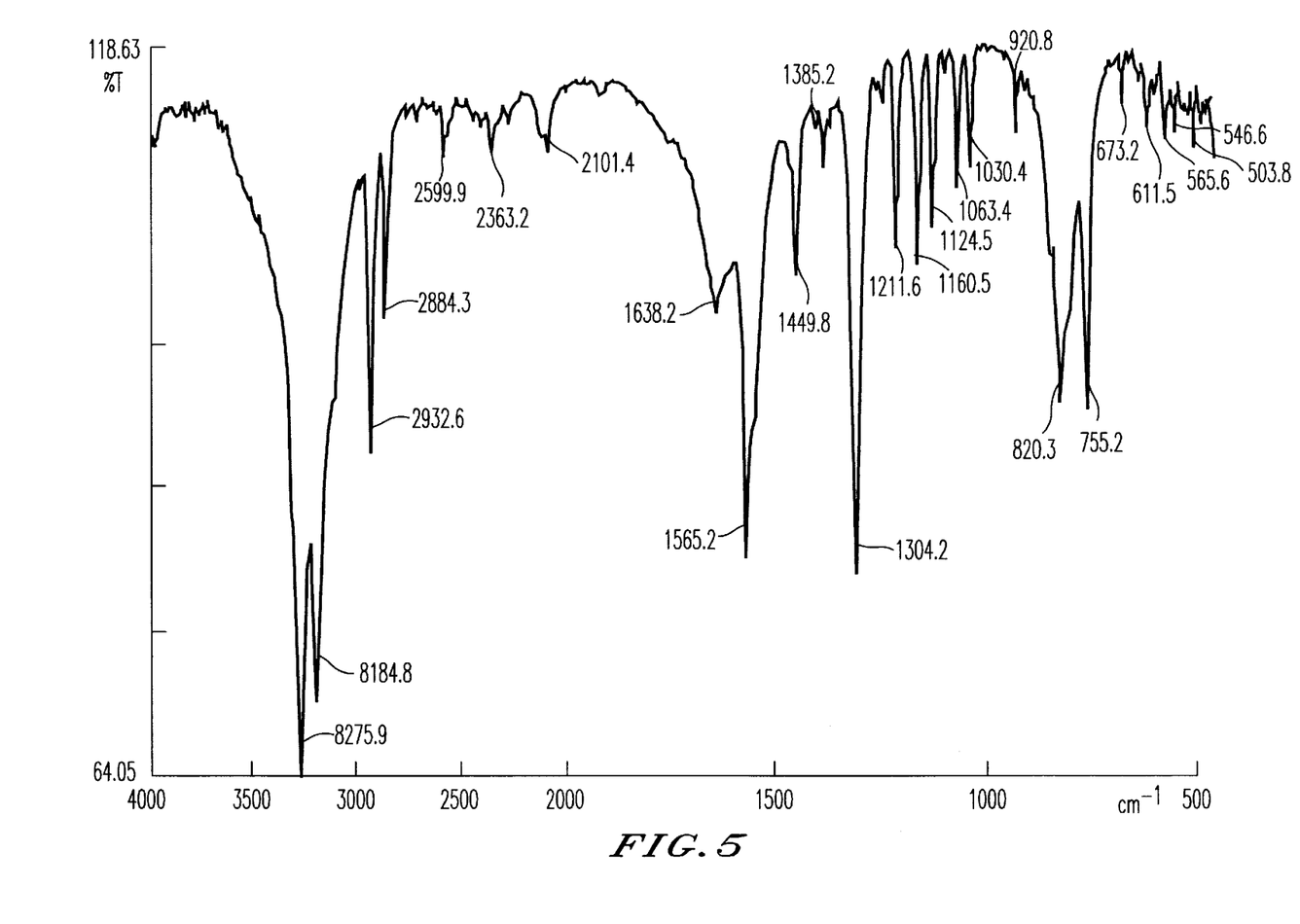
FIG. 5 is an infrared spectrum of the platinum complex: [(cis-diammine) (trans- dichloro) (1R),(2R)- diaminocyclohexane-µ-dichloro-di-Pt(II)-Pt(IV) oxalate.

The infrared absorption spectrum is represented in FIG. 5.

| Elemental analysis: $C_8H_{20}N_4O_4Cl_4Pt_2$ (molar mass = 768 g/mol). | | |
|---|---|---|
| | Calculated | Found |
| C | 12,53% | 12,50% |
| H | 2,61% | 2,75% |
| N | 7,29% | 7,40% |
| Pt | 50,78% | — |

We claim:

1. A compound of formula (I) or (II):

(I)

(II)

wherein:
Y—Y is an amine bidentate ligand of the formula:
NH$_2$—R$_1$NH$_2$ in which R$_1$ is a C$_2$–C$_6$ linear or branched alkylene group or an o-phenylene group; or or a group of the formula:

wherein n=2, 3, 4 or 5; m=0 or 1 and 1=0 or 1;
A$_1$ and A$_2$ represent either two identical ammine monodentate ligands, n-isopropylamine or (C$_3$–C$_7$) cycloalkylamine or they are bonded together thereby forming an amine bidentate ligand of the formula:
NH$_2$—R$_1$—NH$_2$ in which R$_1$ is a C$_2$–C$_6$ linear or branched alkylene group or an o-phenylene group; or a group of the formula:

wherein n=2, 3, 4or 5; m=0 or 1 and 1=0 or 1;
X represents a bridging ligand linking the two platinum atoms selected from the group consisting of Cl, Br, F and I; the dissociable Ld group represents:

either two monodentate B ligands selected from the group consisting of NO$_3^-$, gluconate and glucuronate; or
the bidentate B—B ligand selected from the group consisting of:

wherein R is hydrogen, methyl, ethyl, phenyl or benzyl; and

Hal is a halogen atom selected from the group consisting of Cl, Br, F and I.

2. The compound of formula (I) or (II) according to claim 8, wherein:
Y—Y represents a bidentate ligand selected from the group consisting of ethylene diamine, o-phenylenediamine, trimethylenediamine, 1,2-cyclohexanediamine and 2-(aminomethyl) cyclohexylamine;

X is Cl;

A$_1$ and A$_2$ represent either two ammine monodentate ligands or they are bonded together thereby forming a bidentate ligand selected from the group consisting of ethylenediamine, o-phenylenediamine, trimethylenediamine, 1,2-cyclohexanediamine and 2-(aminomethyl)cyclohexylamine;

Ld is:
either two monodentate B ligands selected from the group consisting of NO$_3^-$, gluconate and glucuronate; or
the bidentate ligand B—B selected from the group consisting of dicarboxylate, sulfate, oxolate, malonate and 1,1-cyclobutanedicarboxylate; and Hal is Cl.

3. The compound of formula (I) or (II) according to claim 1, wherein said compound is selected from the group consisting of:

[(cis-diammine)(1R),(2R)-diaminocyclohexane-μ-dichloro-di-Pt(II)] oxalate,

[(cis-diammine)(1S),(2S)-diaminocyclohexane-μ-dichloro-di-Pt(II)] oxalate,

[(cis-diammine)(1R),(1S)-diaminocyclohexane-μ-dichloro-di-Pt(II)] oxalate,

[bis(1R),(2R)-diaminocyclohexane-μ-dichloro-di-Pt(II)] oxalate,

[(1R),(2R)-diaminocyclohexane (1S),(2S)-diaminocyclohexane-μ-dichloro-di-Pt(II)] oxalate,

[(1R),(2R)-diaminocyclohexane (R),(S)-diaminocyclohexane-μ-dichloro-di-Pt(II)] oxalate

[(cis-diammine) (1R),(2R)-diaminocyclohexane-μ-dichloro-di-Pt(II)] nitrate,

[(cis-diammine) (1S),(2S)-diaminocyclohexane-μ-dichloro-di-Pt(II)] nitrate,

[(cis-diammine) (1R),(1S)-diaminocyclohexane-μ-dichloro-di-Pt(II)] nitrate,

[bis (1R),(2R)-diaminocyclohexane-μ-dichloro-di-Pt(II)] nitrate,

[(1R),(2R)-diaminocyclohexane (1S),(2S)-diaminocyclohexane-μ-dichloro-di-Pt(II)] nitrate,

[(1R),(2R)-diaminocyclohexane (1R),(1S)-diaminocyclohexane-μ-dichloro-di-Pt(II)] nitrate,

[bis (cis-diammine)-μ-dichloro-di-Pt(II)] 1,1-cyclobutanedicarboxylate, and

[(cis-diammine) (transdichloro-(1R),(2R)-diaminocyclohexane-μ-dichloro-Pt(II)-Pt(V)] oxalate.

4. A process for the preparation of a compound of formula (I) or (II), consisting of:

reacting, in an aqueous solution and in equimolar proportion, two mononuclear platinum complexes, one of which is a di-halogenated platinum complex C1 and the other a platinum complex C2 comprising either two monodentate B ligands or one bidentate B—B ligand as defined in claim 1 such that a bridge of the structure:

between the two complexes in which X is as defined in claim 1.

5. The process according to claim 4, which further consists of:
a) dissolving the mononuclear platinum complex C1 in distilled water by the application of heat in a water-bath;
b) dissolving, as in step a), the mononuclear platinum complex C2 in distilled water;
c) mixing the two solutions and boiling the reaction mixture at 80° C.;
d) allowing the reaction mixture to stand at room temperature; and
e) filtering and washing the needle- or scale-shaped pale yellow crystalline precipitate which forms in step d) with warm water and then with alcohol.

6. The process according to claim 5 complex C1 is selected from the group consisting of:

[Pt(II)-cis Cl$_2$ (NH$_3$)$_2$] (cisplatin),

[Pt(II)-Cl$_2$(1S),(2S)-diaminocyclohexane],

[Pt(II)-Cl$_2$(1R),(2R)-diaminocyclohexane],

[Pt(II)-Cl$_2$(1R),(2S)-diaminocyclohexane], and

[Pt(IV)-oxalate trans Cl$_2$ (1R),(2R)-diaminocyclohexane], and the complex C2 is selected from the group consisting of:

[Pt(II)-oxalate (1R),(2R)-diaminocyclohexane] (oxaliplatin),

[Pt(II)-oxalate(1R),(1S)-diaminocyclohexane],

[Pt(II)-(NO$_3$)$_2$ (1R),(2R)-diaminocyclohexane],

[Pt(II)-(NO$_3$)$_2$ (1S),(2S)-diaminocyclohexane],

[Pt(II)-(NO$_3$)$_2$ (1R),(2S)-diaminocyclohexane],

[Pt(II)-cis-diammine 1,1-cyclobutanedicarboxylate] (a carbo-platinum), and

[Pt(IV)-oxalate trans Cl$_2$ (1R),(2R)-diaminocyclohexane].

7. A pharmaceutical composition containing a compound according to any one of claims 1, 2 or 3 as the active principle in combination with a pharmaceutically acceptable carrier.

* * * * *

UNITED STATES PATENT AND TRADEMARK OFFICE
CERTIFICATE OF CORRECTION

PATENT NO.   : 6,153,646
DATED        : November 28, 2000
INVENTOR(S)  : Yoshinori Kidani et al.

Page 1 of 1

It is certified that error appears in the above-identified patent and that said Letters Patent is hereby corrected as shown below:

Column 15,
Line 4, "diaminocyclohexane-μ-dichloro-Pt(II)-Pt(V)] oxalate." should read
-- diaminocyclohexane-μ-dichloro-Pt(II)-Pt(IV)] oxalate. --.

Signed and Sealed this

Twenty-fifth Day of September, 2001

Attest:

NICHOLAS P. GODICI
Attesting Officer   Acting Director of the United States Patent and Trademark Office